United States Patent [19]

Nakai et al.

[11] Patent Number: 4,910,348

[45] Date of Patent: Mar. 20, 1990

[54] PREPARATION OF POLYFLUOROENOLATES

[75] Inventors: Takeshi Nakai, Yokohama; Masamichi Maruta, Kawagoe, both of Japan

[73] Assignee: Central Glass Company, Limited, Ube, Japan

[21] Appl. No.: 104,023

[22] Filed: Oct. 5, 1987

[30] Foreign Application Priority Data

Oct. 6, 1986 [JP] Japan .................................. 61-236233

[51] Int. Cl.$^4$ ...................... C07C 29/68; C07C 33/42; C07C 33/02
[52] U.S. Cl. ...................................... 568/843; 556/54; 556/81; 556/130; 556/182; 558/293; 560/254
[58] Field of Search ........................ 568/842, 843, 293; 556/54, 81, 130, 181, 182

[56] References Cited

U.S. PATENT DOCUMENTS 3,285,975 11/1966 Ahlbrecht ............................ 568/843
3,702,872 11/1972 Regan ................................. 568/842
4,754,082 6/1988 Raab ................................... 568/843

FOREIGN PATENT DOCUMENTS 2196961A 5/1981 United Kingdom ................ 568/843

Primary Examiner—Paul E. Konopka
Attorney, Agent, or Firm—Fleit, Jacobson, Cohn, Price, Holman & Stern

[57] ABSTRACT

Polyfluoroenolates, $R^1CX=CR^2OM$ ($R^1$ is F or a perfluoroalkyl group, $R^2$ is a perfluoroalkyl group, X is F, Cl or Br), are easily formed at good yields by dehydrohalogenation reaction of polyfluoroalcoholates, $R^1CXY-CR^2HOM$ (Y is F, Cl or Br), with a strong base such as, e.g., an alkyl metal or an aryl metal. A typical example of the polyfluoroenolates is lithium pentafluoro-2-propenolate which is obtained from hexafluoro-2-propanolate. A polyfluoroenolate of the above general formula can be converted into another polyfluoroenolate having an alkyl or aryl group in place of the halogen X by reaction with an alkyl or aryl metal.

5 Claims, No Drawings

4,910,348

PREPARATION OF POLYFLUOROENOLATES

BACKGROUND OF THE INVENTION

This invention relates to a novel method of preparing a group of polyfluoroenolates from polyfluoroalcoholates. The polyfluoroenolates are, or will be useful as intermediate materials for synthesizing various organic fluoro-compounds.

In organic synthetic chemistry, the chemistry of enolates is an important field having wide applications. However, polyfluoroenolates have hitherto received but scant attention in both preparation and applications thereof.

It is known that lithium pentafluoro-2-propenolate is obtained by reacting pentafluoro-2-propenol with, for example, butyl lithium at a low temperature such as −78° C. (Zh. Org. Khim., 12, 1379 (1976) ). Pentafluoro-2-propenol is a tautomer of pentafluoroacetone and, in laboratory, can be isolated in the enol form by distillation although the enol form is metastable state. Actually, however, it is difficult to obtain pentafluoro-2-propenol directly from pentafluoroacetone because aldol condensation of the isolated enol soon takes place. Therefore, it was devised to obtain pentafluoro-2-propenol by thermal decomposition or acid decomposition of a pentafluoro-2-propenyldialkyl-phosphate which is prepared by the Perkov reaction of chloropentafluoroacetone with a dialkyl- or trialkyl-phosphate (Zh. Org. Khim., 11, 1370(1975) ). However, by this process the total yield of the propenol is only 30–40%, and the high toxicity of chloropentafluoroacetone offers a serious problem to practical operations. Analogous difficulties are involved also in the preparation of other polyfluoroenols or polyfluoroenolates.

SUMMARY OF THE INVENTION

It is an object of the present invention to provide a method for easily preparing polyfluoroenolates including pentafluoro-2-propenolates at fairly high yields.

According to the invention, there is provided a method of preparing a polyfluoroenolate represented by the general formula (1), $$R^1CX=CR^2OM \tag{1}$$

wherein $R^1$ represents a fluorine atom or a perfluoroalkyl group, $R^2$ represents a perfluoroalkyl group, M represents a cation of Li, Na, K, Mg, Zn, B, Al, Ti or Sn, and X represents F, Cl or Br, the method being characterized in that a polyfluoroalcoholate represented by the general formula (2) is reacted with a strong base to undergo dehydrohalogenation:

$$\underset{R^1CXY-CHOM}{\overset{R^2}{|}} \tag{2}$$

wherein $R^1$, $R^2$, M and X are as defined above with respect to the general formula (1), and X represents F, Cl or Br on condition that X represents F when Y represents F.

The strong base used in this method can be selected, for example, from alkyl metals, aryl metals, metal dialkylamides and metal bistrialkylsilylamides.

Ordinarily dehydrohalogenation reactions can be carried out under relatively mild conditions, but in the cases of dehydrohalogenation of alcoholates it is necessary to use a strong base because dianions are intermediately formed. In general it is difficult to control the reaction between a polyfluoro-compound and a base because in some cases the expected reaction hardly takes place and in some other cases the reaction product further reacts with the base by reason of high activity of the double bond produced by dehydrohalogenation. Therefore, when a strong base is used particular care has to be directed to selection of a reagent low in nucleophilic tendency and also to determination of the reaction conditions including employment of a sufficiently low reaction temperature.

Despite the foregoing facts, we found that polyfluoroenolates represented by the general formula (1) are very stable, and are stable even at room temperature, and that in the cases of these polyfluoroenolates the reactivity of the double bond produced by the dehydrohalogenation reaction to nucleophilic reagents are suppressed by the enolate anion, and consequently the present invention has been made.

As is known, polyfluoroalcoholates for use in this invention can be obtained by reaction of polyfluoroalcohols with an alkyl metal, aryl metal or a metal hydride, or by reduction of polyfluoroketones with a metal hydride, or by reaction of polyfluoroalkyl metals with polyfluoroaldehyde or polyfluoroacyl halide.

It is possible to convert a polyfluoroenolate prepared by the method according to the invention into another polyfluoroenolate represented by the general formula (3) by reacting the former polyfluoroenolate with an organic metal compound represented by the general formula (4):

$$R^1R^3C=CR^2Om \tag{3}$$

wherein $R^1$, $R^2$ and M are as defined hereinbefore with respect to the general formula (1), and $R^3$ represents an alkyl group which may optionally have an inactive substituent or an aryl group which may optionally have an inactive substituent, $$R^3M' \tag{4}$$

wherein $R^3$ is as defined above, and M' represents Li, Na, K or Mg.

Polyfluoroenolates obtained by the present invention can be esterified or etherified by known reactions, and the enols liberated by treatment with hydrogen chloride can be converted into various derivatives. Like ordinary enolates, the polyfluoroenolates can be subjected to aldol condensation reactions with ketones or aldehydes. Accordingly it is possible to obtain from the polyfluoroenolates various kinds of organic fluoro-compounds including ones probably useful as intermediates of medicines or agricultural chemicals.

DESCRIPTION OF THE PREFERRED EMBODIMENTS

In the method according to the invention an indispensable reactant is a strong base which is preferably selected from alkyl metals, aryl metals, metal dialkylamides and metal bistrialkylsilylamides. Good examples of such metal compounds are methyl lithium, butyl lithium, phenyl lithium, butyl sodium, phenyl sodium, butyl magnesiumhalides, phenyl magnesiumhalides and lithium diiospropylamide. In most cases it suffices to use 1 mol of such a strong base per 1 mol of the polyfluoroalcoholate, but there arises no problem by using the base in some excess.

The reaction of a polyfluoroalcoholate of the general formula (2) with a strong base is carried out in an organic liquid medium which is inactive to the base. For example, the liquid medium is an ether such as diethyl ether or tetrahydrofuran or a hydrocarbon such as hexane or benzene. It is suitable to carry out this reaction at a temperature in the range from $-80°$ C. to $50°$ C., and preferably from $10°$ to $30°$ C.

As mentioned hereinbefore, a polyfluoroenolate of the general formula (3) can be prepared by subjecting a polyfluoroenolate of the general formula (1) to addition-elimination reaction with an alkyl or aryl metal of the general formula (4). It is suitable to carry out this reaction at a temperature in the range from $-10°$ C. to $100°$ C., and preferably from room temperature to $50°$ C. It is possible to perform the initial reaction to form a polyfluoroenolate of the general forumula (1) and the reaction for conversion into a polyfluoroenolate of the general formula (3) successively.

The invention is further illustrated by the following nonlimitative examples.

EXAMPLE 1

In a nitrogen gas atmosphere, 0.84 g (5 millimol) of hexafluoro-2-propanol and 5 ml of tetrahydrofuran were injected with a syringe into a dry 20-ml three-necked flask provided with thermometer, rubber septum and cooling pipe and cooled to $-78°$ C. by using a dry ice-acetone bath. Maintaining the temperature in the flask below $-75°$ C., 6.8 ml of 1.6M solution of n-butyl lithium in hexane was dropped into the flask in 5 min by using a syringe, whereby 10.9 mmol of n-butyl lithium was introduced. After that the bath was changed to a water bath to which ice was added according to the need to carry out reaction between hexafluoro-2-propanol and n-butyl lithium at $0°$ C. for 1 hr.

By $^{19}$F-NMR anaylsis (internal standard: benzotrifluoride) of the reaction product, formation of lithium pentafluoro-2-propenolate at 96.5% yield was confirmed. After dissipating the solvent by using an evaporator, the product was subjected to $^{19}$F-NMR analysis using diethylether as solvent. The results: $-8.0$ (CF$_3$, d, d), 30.3 (F—t, d, br), 41.3 (F—c, d, br), JCF$_3$—F—t=9.4 Hz, JCF$_3$—F—c=22.6 Hz, JF—F=88.4 Hz. Literature shows: $-8.0$ (CF$_3$), 31.9 (F—t), 40.9 (F—c), JCF$_3$—F—t=9.6 Hz, JCF$_3$—F—c=29.6 Hz, JF—F=97.6 Hz (Zh. Org. Khim., 12, 1379(1976) ).

Treatment of thus obtained lithium pentafluoro-2-propenolate with hydrogen chloride gas gave pentafluoro-2-propenol. $^{19}$F-NMR: $-7.7$ (CF$_3$, d, d), 17.6 (F—t, q, d), 25.8 (F—c, q, d), JCF$_3$—F—t=9.7 Hz, JCF$_3$—F—c=24.2 Hz, JF—F=56.2 Hz.

EXAMPLE 2

The process of forming lithium pentafluoro-2-propenolate in Example 1 was repeated. Following the above described reaction at $0°$ C. for 1 hr, 0.84 g (6 mmol) of benzoyl chloride was added to the reaction system and stirring was continued for 30 min at room temperature. By $^{19}$F-NMR analysis (internal standard: benzotrifluoride), formation of pentafluoro-2-propenylbenzoate at 99.2% yield was confirmed.

After adding 0.5N hydrochloric acid to the reaction product, pentafluoro-2-propenylbenzoate was isolated by performing extraction with ethyl acetate twice and washed with saturated aqueous solution of sodium chloride. The washing was subjected to extraction with ethyl acetate, and the extracts were collected together and dried with magnesium sulfate. After filtration the dried extract was distilled to collect a distillate at $46°–48°$ C./5 mmHg. As the result 1.11 g (yield 88.1%) of pure pentafluoro-2-propenylbenzoate was obtained. $^{19}$F—NMR ($\delta$CH$_3$COOH, neat): $-10.7$ (CF$_3$, d, d), 6.5 (F—t, q, d), 15.0 (F—c, q, d), JCF$_3$—F—t=7.9 Hz, JCF$_3$—F—c=17.9 Hz, JF—F=27.3 Hz. $^{1}$H—NMR (CDCl$_3$): 7.4–8.3 (Ar).

EXAMPLE 3

In the process of Example 2 the temperature and time of the reaction between hexafluoro-2-propanol and n-butyl lithium were varied as shown in Table 1. Otherwise the entire process of Example 2 was repeated in every run. As shown in the same table, the changes in the reaction conditions resulted in changes in the yield of pentafluoro-2-propenylbenzoate measured after the final distillation operation. That is, in some cases hexafluoro-2-propylbenzoate was found together with or instead of pentafluoro-2-propenylbenzoate. The proportion of these two kinds of reaction products was determined by $^{19}$F-NMR analysis.

TABLE 1

| | Reaction Temp. (°C.) | Reaction Time (hr.) | yield (%) | Reaction Product pentafluoro-2-propenyl-benzoate (%) | hexafluoro-2-propyl-benzoate (%) |
|---|---|---|---|---|---|
| Run A | 24 | 0.5 | 83 | 100 | 0 |
| Run B | $-40$ | 4 | 75 | >99 | <1 |
| Run C | $-50$ | 4 | 86 | 90 | 10 |
| Run D | $-78$ | 4 | 79 | 37 | 63 |
| Run E | $-78$ | 0.5 | 82 | 0 | 100 |

EXAMPLE 4

The entire process of Example 2 was repeated except that trifluoroacetyl chloride was used in place of benzoyl chloride.

As the result pentafluoro-2-propenyltrifluoroacetate was obtained at 71% yield. $^{19}$F—NMR: $-4.3$ (CF$_3$, s), $-20.2$ (CF$_3$, d, d), 8.2 (F—t, q, d), 23.7 (F—c, q, d), JCF$_3$—F—t=8.5 Hz, JCF$_3$—F—c=19.8 Hz, JF—F=23.5 Hz.

EXAMPLE 5

Lithium pentafluoro-2-propenolate was formed by the operations described in Example 1, and the solvent was completely removed by first using an evaporator and then a vacuum pump. To the residual product 0.6 g (5.5 mmol) of chlorotrimethylsilane was added while cooling by iced water, and the resultant mixture was left standing at room temperature for 30 min. After that a trap-to-trap operation was made to thereby collect trimethylsilylpentafluoro-2propenolate. $^{19}$F—NMR: $-8.5$ (CF$_3$, d, d), 17.8 (F—t, q, d), 27.7 (F—c, q, d), JCF$_3$—F—t=8.6 Hz, JCF$_3$—F—c=21.6 Hz, JF—F=51.7 Hz.

EXAMPLE 6

In repeating the process of Example 1 to form lithium pentafluoro-2-propenolate, the quantity of n-butyl lithium was increased to 15 mmol and the reaction was carried out at room temperature for 4 hr. In repeating the post-treatment described in Example 2, acetyl chloride was used in place of benzoyl chloride. As the result 0.8 g (yield 70.5%) of tetrafluoro-2-heptene-2-yl acetate (b.p. 79°–80° C. at 30 mmHg) was obtained.

In this product the proportion of E-form to Z-form was 72:28. Elementary analysis gave the following result. Calculated as $C_9H_{12}O_2F_4$: C 47.37%, H 5.30%. Found: C 47.56%, H 5.35%. $^{19}F$—NMR: E-form; $-12.6$ ($CF_3$, d), 40.7 (F, m), $JCF_3-F=16.6$ Hz; Z-form; $-13.7$ ($CF_3$, d), 26.0 (F,m), $JCF_3-F=8.5$ Hz. $^1H$—NMR: E-Z mixture; 2.20 (s, 3H), 0.96 (t, 3H), 1.50 (m, 6H).

EXAMPLE 7

In the process of Example 6 the temperature and time of the reaction between hexafluoro-2-propanol and n-butyl lithium were varied as shown in Table 2. Otherwise the entire process of Example 6 was repeated in every run. As shown in the same table, the changes in the reaction conditions resulted in changes in the yield of tetrafluoro-2-heptene-2-yl acetate and the proportion between the isomers in the product analyzed by $^{19}F$—NMR.

TABLE 2

|  | Reaction Temp. (°C.) | Reaction Time (hr.) | Reaction Product |  |  |
|---|---|---|---|---|---|
|  |  |  | Yield (%) | E-form (%) | Z-form (%) |
| Run A | 60 | 3 | 30 | 0 | 100 |
| Run B | 40 | 4 | 58 | 60.3 | 39.7 |
| Run C | 0 | 7 | 62 | 72.5 | 27.5 |
| Run D | −10 | >12 | 63 | 75.5 | 24.5 |
| Run E | −20 | >12 | 0 | — | — |

EXAMPLE 8

Lithium pentafluoro-2-propenolate was formed by the same operations as in Example 1, and 2.5 ml of 2M solution of phenyllithium in a mixture of cyclohexane and ether was added, followed by stirring at room temperature for one night. After that 0.47 g (6 mmol) of acetyl chloride was added and the resultant mixture was stirred for 30 min. Then the post-treatment described in Example 2 was performed, and the treated product was purified by using a silica gel column (eluate: mixture of ethyl acetate and hexane (10:1)). As the result 0.78 g (yield 66.2%) of 1-phenyltetrafluoro-2-propenylacetate was obtained.

In this product, E:Z was 68:32. Elementary anaylsis: calculated as $C_{10}H_9F_5O_2$; C 53.24%, H 3.25%; found; C 53.50%, H 3.38%.

EXAMPLE 9

In repeating the process of Example 8, the phenyllithium solution was replaced by a solution of phenylmagnesium bromide, which was prepared from 0.24 g (10 mmol) of magnesium and 1.25 g (8 mmol) of bromobenzene, in tetrahydrofuran, and the reaction was carried out at 50° C. for 24 hr. By column treatment, 1-phenyltetrafluoro-2-propenylacetate (E:Z=87:13) was obtained at 48% yield and pentafluoro-2-propenylacetate at 24% yield.

$^{19}F$—NMR: E-form; $-12.3$ ($CF_3$, d), 43.3 (F, q), $JCF_3-F=15.0$ Hz; Z-form; $-13.7$ ($CF_3$, d), 15.3 (F, q), $JCF_3-F=7.5$ Hz. $^1H$—NMR: E-form; 2.20 ($CH_3$, s, 3H), 7.0–7.7 (Ar, 5H); Z-form; 2.13 ($CH_3$, s, 3H), 7.5–7.6 (Ar, 5H).

EXAMPLE 10

In repeating the process of Example 8, the phenyllithium solution was replaced by a solution of ethylmagnesium bromide, which was prepared from 0.24 g (10 mmol) of magnesium and 0.87 g (8 mmol) of bromoethane, in tetrahydrofuran, and the reaction was carried out at 50° C. for 24 hr. In this case, benzoyl chloride was used in place of acetyl chloride for esterification. The post-treatment was as mentioned in Example 8. As the result tetrafluoro-2-pentene-2yl benzoate (E:Z=70.3:29.7) was obtained at 67.7% yield and pentafluoro-2-propenylbenzoate at 11.5% yield.

$^{19}F$—NMR: E-form; $-11.6$ ($CF_3$, t, d), 42.0 (F, q, t), $JCF_3-F=16.6$ Hz, $JF-CH_2=18.8$ Hz; Z—form; $-13.0$ ($CF_3$, t, d), 28.0 (F, q, t), $JCF_3-F=8.5$ Hz, $JF-CH_2=21.6$ Hz.

EXAMPLE 11

A Grignard solution was prepared by using 0.48 g (20 mmol) of magnesium, 3.14 g (20 mmol) of bromobenzene and 10 ml of tetrahydrofuran. At room temperature 1.68 g (10 mmol) of hexafluoro-2-propanol was dropped into the Grignard solution in 5 min, and the resultant mixture was stirred for 1 hr at room temperature to thereby carry out dehydrohalogenation reaction. Then 1.40 g (10 mmol) of benzoyl chloride was added to the reaction system, and the post-treatment described in Example 2 was performed. By $^{19}F$—NMR analysis, formation of pentafluoro-2-propenylbenzoate at 10.6% yield was confirmed. The remainder of the product was hexafluoro-2-propylbenzoate.

EXAMPLE 12

A Grignard solution was prepared by using 0.48 g (20 mmol) of magnesium, 2.74 g (20 mmol) of 1-bromobutane and 10 ml of tetrahydrofuran. using this Grignard solution the process of Example 11 was repeated. As the result pentafluoro-2-propenylbenzoate was formed at 10.8% yield and tetrafluoro-2-heptene-2-yl benzoate at 1.2% yield. The remainder was hexafluoro-2-propylbenzoate.

EXAMPLE 13

Lithium pentafluoro-2-propenolate was formed by the same operations as in Example 1. Then 0.74 g (7 mmol) of benzaldehyde was dropped by a syringe into the reaction system maintained at 0° C., and the resultant mixture was stirred for 15 min. After adding 0.5N hydrochloric acid to the reaction system, the reaction product was extracted with ethyl acetate and washed with saturated aqueous solution of sodium chloride. The washing was subjected to extraction with ethyl acetate, and the extracts were collected together and dried with magnesium sulfate. After filtration the dried extract was concentrated and purified by using a silica gel column (eluate: mixture of ethyl acetate and hexane (10:1)). As the result 0.91 g (yield 72%) of pentafluorohydroxyoxetane (m.p. 90°–91° C.) was obtained.

Elementary analysis: calculated as $C_{10}H_7O_2F_5$; C 47.41%, H 2.78%; found; C 47.50%, H 3.05%. $^{19}F$—NMR: 3 ($CF_3$, d, d), 38.3 ($F_b$, d, q, d), 51.0 ($F_a$, q, d, d), $JCF_3-F_a=9.4$ Hz, $JCF_3-F_b=11.3$ Hz, $JF_a-F_b=254$ Hz, $JF_a-H=19.6$ Hz, $JF_b-H=2.3$ Hz. $^1H$—NMR ($CDCl_3$): 5.4 (d, d, 1H), 5.6 (OH, 1H), 7.2–7.6 (Ar, 5H).

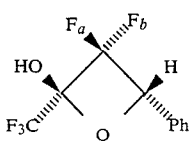

EXAMPLE 14

In repeating the process of Example 13, 0.84 g (7 mmol) of acetophenone was used in place of benzaldehyde, and the reaction time after addition of acetophenone was extended to 30 min. As the result 11.7 g (yield 82%) of purified 4-hydroxy-4-phenylpentafluoro-2-pentanone hydrate (m.p. 64° C.) was obtained. Elementary analysis: calculated as $C_{11}H_{11}O_3F_5$; C 46.16%, H 3.87%, found; C 46.27%, H 4.04%. $^{19}F$—NMR: 3.2 ($CF_3$, t), 38.5 ($CF_2$, m, q), $J_{CF_3-CF_2} = 11.3$ Hz. $^1H$—NMR ($CDCl_3$): 1.86 ($CH_3$, t), 3.57 (OH, 2H), 5.36 (OH, 1H), 7.4–7.7 (Ar, 5H).

EXAMPLE 15

The process of Example 14 was repeated except that 0.35 g (6 mmol) of acetone was used in place of acetophenone. As the result 0.83 g (yield 74%) of purified 4-hydroxy-4-methyl-pentafluoro-2-pentanone hydrate (m.p. 58°–59° C.) was obtained. Elementary analysis: calculated as $C_6H_9F_5O_3$; C 32.15%, H 4.05%; found; C 32.04%, H 3.74%. $^{19}F$—NMR: 4.0 ($CF_3$, t), 42.8 ($CF_2$, q), $J_{CF_3-CF_2} = 12.2$ Hz. $^1H$—NMR ($CDCl_3$): 1.53 ($CH_3$, 6H), 4.13 (OH, 1H), 5.86 (OH, 2H).

What is claimed is:

1. A method of preparing a polyfluoroenolate represented by the formula (1), $$R^1CX=CR^2OM \quad (1)$$

wherein $R^1$ represents a fluorine atom or a perfluoroalkyl group, $R^2$ represents a perfluoroalkyl group, X represents F, Cl or Br, and M represents a cation selected from the group consisting of Li, Na and K, comprising reacting a polyfluoroalcoholate represented by the formula (2) with a strong base selected from the group consisting of alkyl metals, aryl metals, metal dialkylamides and metal bistrialkylsilylamides at a temperature of from $-80°$ C. to $50°$ C.:

wherein $R^1$, $R^2$, X and M are as defined above with respect to formula (1), and Y represents F, Cl or Br, with the proviso that X represents F when Y represents F;

the amount of said strong base being at least one mole per mole of the polyfluoroalcoholate.

2. A method according to claim 1, wherein said strong base is selected from the group consisting of methyl lithium, butyl lithium, phenyl lithium, butyl sodium, phenyl sodium and lithium diisopropylamide.

3. A method according to claim 1, wherein said polyfluoroalcoholate is a hexafluoro-2-propanolate and said polyfluoroenolate is a pentafluoro-2-propenolate.

4. A method according to claim 1, wherein the reaction is carried out in an organic liquid medium which is inactive to said base.

5. A method according to claim 1, wherein said temperature is in the range from 10° to 30° C.

* * * * *